US006394798B1

(12) United States Patent
Huff et al.

(10) Patent No.: US 6,394,798 B1
(45) Date of Patent: May 28, 2002

(54) UNITARY METAL INJECTION MOLDED ORTHODONTIC BRACKET

(75) Inventors: Stephen M. Huff, San Diego; Lindsay W. Brehm, Encinitas, both of CA (US)

(73) Assignee: Ortho Organizers, San Marcos, CA (US)

(*) Notice: Subject to any disclaimer, the term of this patent is extended or adjusted under 35 U.S.C. 154(b) by 0 days.

(21) Appl. No.: 09/652,397

(22) Filed: Aug. 31, 2000

(51) Int. Cl.[7] .............................................. A61C 7/12
(52) U.S. Cl. ............................ 433/8; 433/10; 433/13
(58) Field of Search .......................... 433/8, 9, 10, 13, 433/15, 16, 17

(56) References Cited

U.S. PATENT DOCUMENTS

| | | | | |
|---|---|---|---|---|
| 4,355,975 A | * | 10/1982 | Fujita | 433/11 |
| 4,582,487 A | * | 4/1986 | Creekmore | 433/8 |
| 5,062,794 A | | 11/1991 | Miura | 433/10 |
| 5,160,261 A | | 11/1992 | Peterson | 433/8 |
| 5,161,969 A | * | 11/1992 | Pospisil et al. | 433/8 |
| 5,232,361 A | * | 8/1993 | Sachdeva et al. | 433/8 |
| 5,252,066 A | * | 10/1993 | Fairhurst | 433/8 |
| 5,302,116 A | | 4/1994 | Viazis | 433/8 |
| 5,395,237 A | * | 3/1995 | Pospisil et al. | 433/8 |
| 5,456,599 A | | 10/1995 | Hanson | 433/8 |
| 5,470,228 A | | 11/1995 | Franseen et al. | 433/8 |
| D367,116 S | | 2/1996 | Viazis | D24/180 |
| 5,595,484 A | * | 1/1997 | Orikasa et al. | 433/8 |
| 5,616,026 A | * | 4/1997 | Cash | 433/8 |
| 5,885,074 A | * | 3/1999 | Hanson | 433/13 |

* cited by examiner

*Primary Examiner*—John J. Wilson
*Assistant Examiner*—Melba Bumgarner
(74) *Attorney, Agent, or Firm*—Fulwider Patton Lee & Utecht, LLP

(57) ABSTRACT

The present invention accordingly provides for an orthodontic bracket having a plurality of tiewings and a plurality of posts extending in the mesial/distal direction. The plurality of tiewings may be located on the occlusal side of the orthodontic bracket, and may include a center post between the tiewings, for placement reference and ligation of the orthodontic bracket. A hook may be provided on the gingival side of the orthodontic bracket for anchorage and ligating of the orthodontic bracket, and the tiewings may be provided on the occlusal and gingival side of the orthodontic bracket. The posts may be provided on the gingival side, or on the occlusal and gingival sides of the orthodontic bracket, to assist in bracket placement and to direct a ligature over or under an archwire occupying the archwire slot during treatment, as desired. A biocompatible wire clip ligature and biocompatible cap ligature are also provided for retaining the archwire in the archwire slot, and the bonding base may have a recessed number for identification of the tooth location of the orthodontic bracket molded therein.

27 Claims, 9 Drawing Sheets

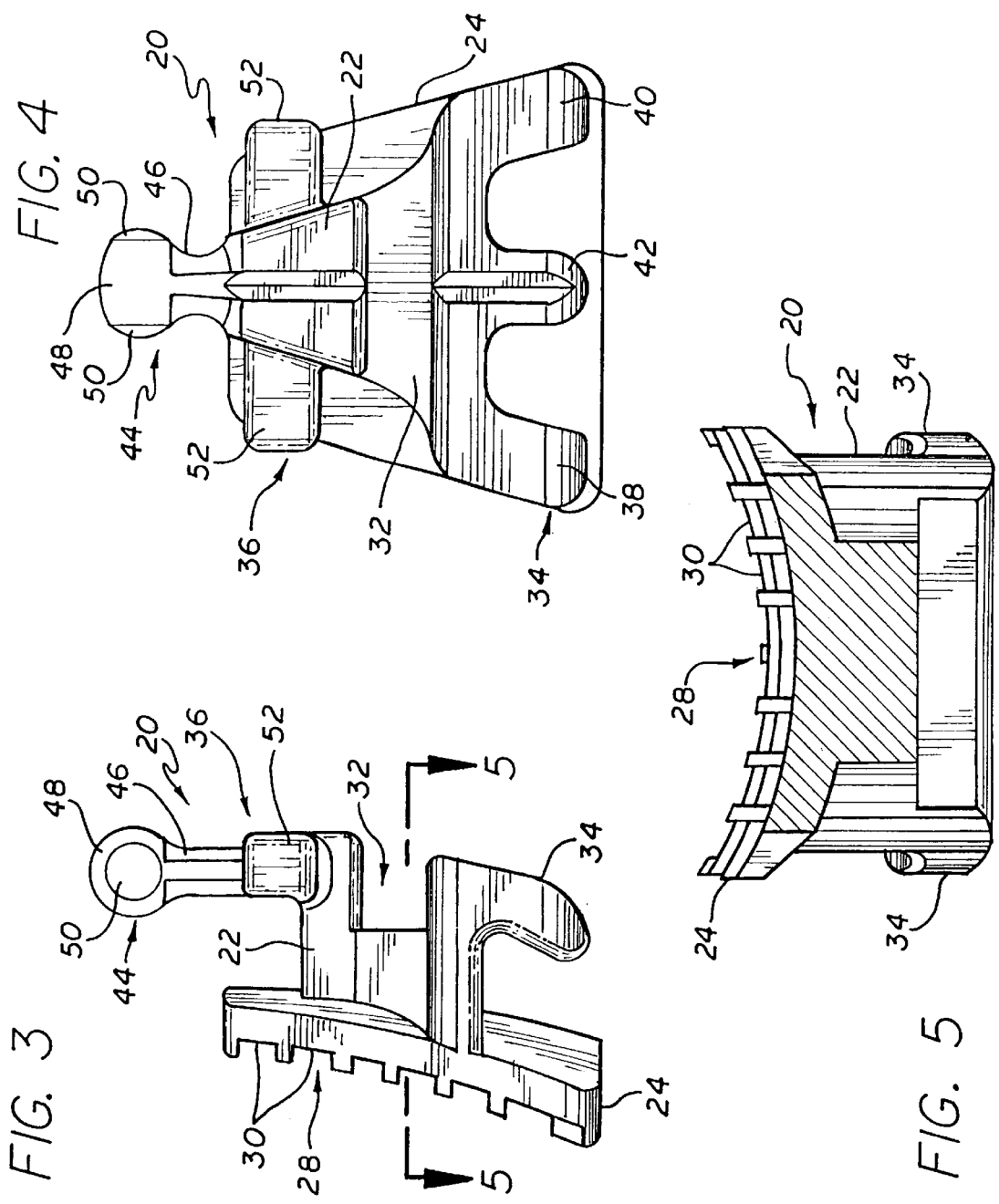

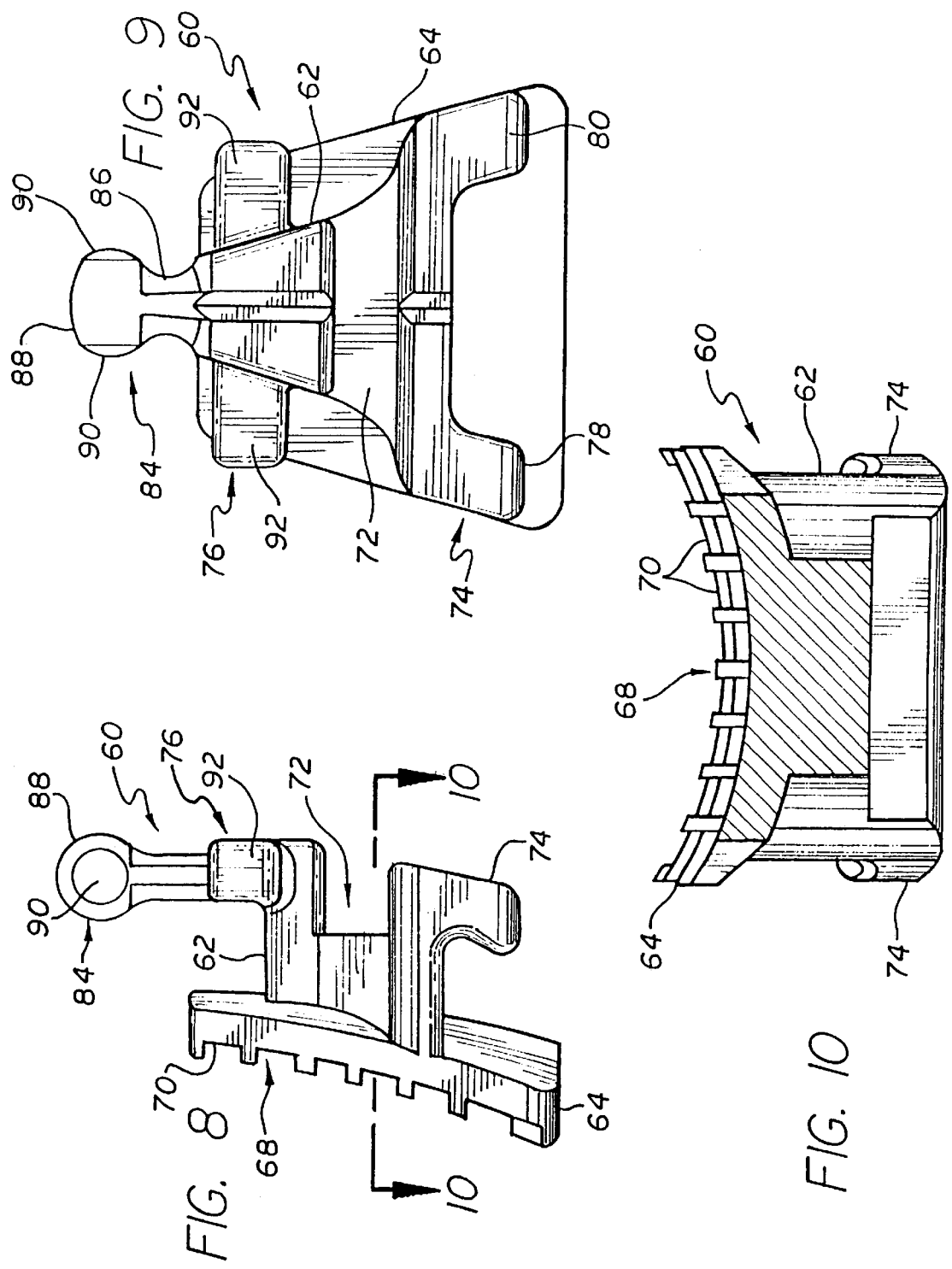

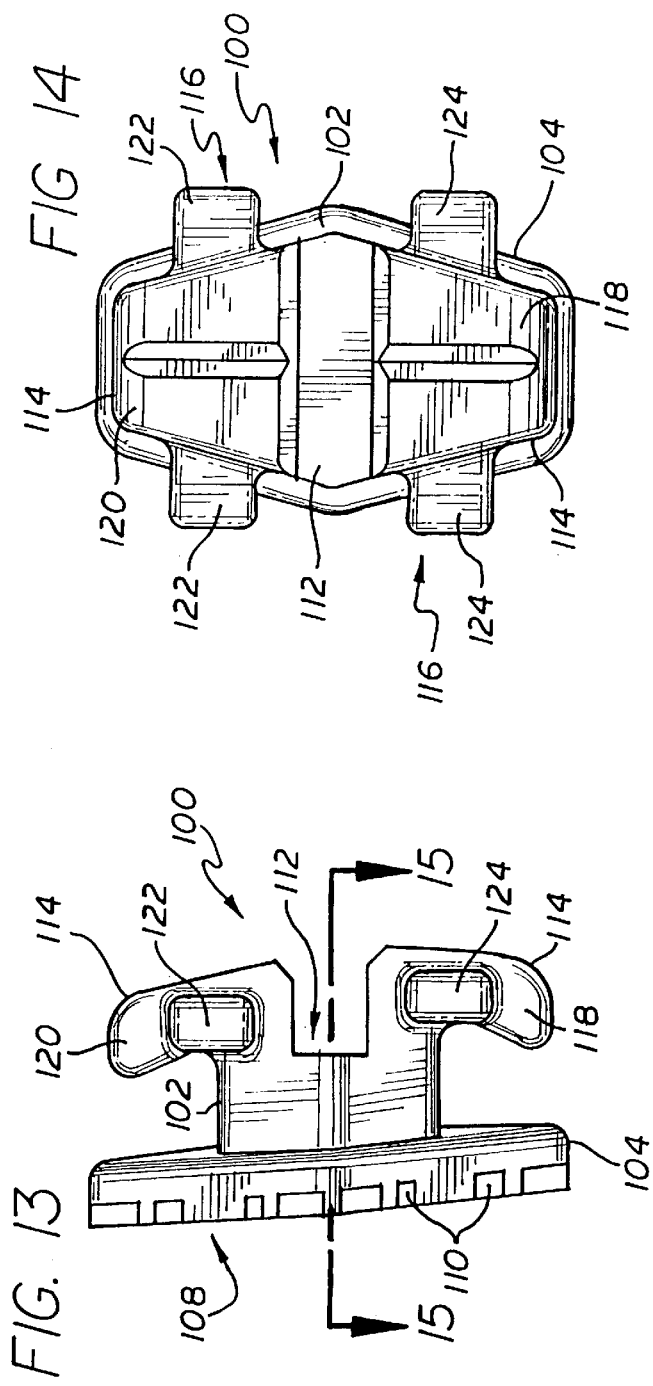

UNITARY METAL INJECTION MOLDED ORTHODONTIC BRACKET

BACKGROUND OF THE INVENTION

1. Field of the Invention

This invention relates generally to orthodontic appliances, and more particularly concerns an orthodontic bracket allowing ligature ties to be placed on the orthodontic bracket so as to control the friction between an archwire and the bracket.

2. Description of Related Art

Orthodontic appliances, such as brackets, buccal tubes and the like, are typically applied to teeth by adhering the appliances to the surface of the teeth to orient the teeth by the application of forces on the teeth by such orthodontic appliances. Such appliances typically include archwire portions for receiving an archwire and ligature elastic bands to provide corrective forces to straighten and reposition the teeth. The orthodontic appliances include a base portion adapted to conform to the shape of the teeth to which they are applied, and elastic or wire ligature ties are used to hold the archwire in the archwire slot during initial and intermediate stages of treatment. However, tooth movement and straightening can be slowed by friction caused by such elastic or wire ligature ties, increasing the duration of orthodontic treatment. It is thus desirable for such ligature ties to remain above the archwire particularly during such initial and intermediate stages of treatment when the most significant amount of movement and straightening of teeth typically occurs, in order to allow the archwire to slide freely with minimal friction when such movement is necessary to facilitate tooth movement and straightening.

One known orthodontic bracket provides a base, a pair of opposing tie wings including a gingivally extending tie wing and an occlusally extending tie wing, an archwire slot defined in a vertical element between the pair of opposing tie wings, and a hook having a ball portion adapted to be oriented to extend toward the gingival side. A horizontal element is connected to the vertical element and includes opposing first and second ends extending away from the vertical element defining a pair of spaced-apart wire engaging points engageable with the arch wire for enabling rotational control of the bracket during use. The ends of the horizontal member also define horizontally extending wings for engaging stretched elastomeric modules to enhance rotational control. The slot in the vertical element has its lower surface vertically spaced from the horizontal element to limit contact between the arch wire and the horizontal element.

Another known type of orthodontic appliance provides for a bracket having one or two pairs of opposing gingival/occlusal tie-wings projecting on either side of an archwire slot, with gingival/occlusal hooks. The bracket includes four shoulders on the free ends of the bracket, with two shoulders being located on opposite sides of the archwire slot with respect to each other on the mesial end of the appliance, and the other two shoulders being located on opposite sides of the archwire slot with respect to each other on the distal end of the appliance. Each shoulder is adapted to support a ligature spaced apart from the archwire in the archwire slot to permit the appliance to move relative to the archwire during orthodontic treatment.

Another type of orthodontic appliance provides for a bracket having a pair of opposing T-shaped tie wings, with an archwire slot between the tie wings. Notches are provided on each of the mesial and distal sides of a center leg of each of the T-shaped tie wings for receiving a ligating device. A T-shaped hook may also be provided as an extension to the center leg of one of the T-shaped wings, to facilitate retention of a traction device. The tie wings include ligating support notches having a sloped portion extending toward the slot extending from the gingival or occlusal periphery of the tie wing, and having a curvilinear, concave configuration to reduce frictional engagement between an archwire positioned in the slot and a ligating device positioned across the archwire slot. The archwire slot may also include convex sidewall and/or floor portions to reduce frictional engagement between the archwire and bracket. However, it would be desirable to provide an orthodontic appliance that also allows full contact of the ligature ties and archwire when desired, such as in the finishing stages of treatment. It would also be desirable to provide the orthodontic appliance with additional features to assist the doctor in orienting the orthodontic appliance to its optimal position, and to allow the ligature to be placed spaced apart from or next to the archwire depending on the friction desired. The present invention meets these and other needs.

SUMMARY OF THE INVENTION

Briefly, and in general terms, the present invention provides for an orthodontic bracket that permits a ligature tie to be placed on the orthodontic bracket spaced apart from an archwire for the bracket to allow the archwire to slide freely with respect to the orthodontic bracket with minimal friction, and that permits a ligature tie to be placed on the orthodontic bracket with full contact between the ligature tie and archwire, as desired. The orthodontic bracket also includes features to assist an orthodontist in orienting the orthodontic appliance to an optimal position, and to allow the orthodontist the options of placing the ligature tie in different positions depending on the desired degree of friction between the ligature tie and the archwire.

The present invention accordingly provides for an orthodontic bracket having a body comprising a plurality of tiewings, and a plurality of posts extending in the mesial/distal direction. In a presently preferred embodiment, the plurality of tiewings are located on the occlusal side of the orthodontic bracket, and in one presently preferred aspect, may also include a center post between the tiewings, for placement reference and ligation of the orthodontic bracket. In a presently preferred aspect, a hook may be provided on the gingival side of the orthodontic bracket for anchorage and ligating of the orthodontic bracket. In another presently preferred embodiment, tiewings may be provided on the occlusal and gingival side of the orthodontic bracket. The plurality of posts extending in the mesial/distal direction may be provided on the gingival side, or on the occlusal and gingival sides of the orthodontic bracket, to assist in bracket placement and to direct an elastomeric or wire ligature over or under an archwire occupying the archwire slot during treatment, as desired. The bracket is preferably comprised of cobalt chromium alloy, or may alternatively be comprised of another suitable biocompatible alloy.

In another presently preferred aspect of the invention the bonding base of the orthodontic bracket may be formed to have a molded recessed number for identification of the tooth location for the orthodontic bracket. In another presently preferred aspect, a biocompatible wire clip ligature, or a biocompatible cap ligature, may be provided to fit over the orthodontic bracket to serve as a ligature to retain an archwire in the archwire slot of the orthodontic bracket.

These and other aspects and advantages of the invention will become apparent from the following detailed description and the accompanying drawings, which illustrate by way of example the features of the invention.

BRIEF DESCRIPTION OF THE DRAWINGS

FIG. 3 is a front elevational view of the orthodontic bracket of FIG. 1;

FIG. 4 is a plan view of the orthodontic bracket of FIG. 1;

FIG. 5 is a sectional view of the orthodontic bracket taken along line 5—5 of FIG. 3;

FIG. 8 is a front elevational view of the orthodontic bracket of FIG. 6;

FIG. 9 is a plan view of the orthodontic bracket of FIG. 6;

FIG. 10 is a sectional view of the orthodontic bracket taken along line 10—10 of FIG. 8;

FIG. 13 is a front elevational view of the orthodontic bracket of FIG. 11;

FIG. 14 is a plan view of the orthodontic bracket of FIG. 11;

FIG. 15 is a sectional view of the orthodontic bracket taken along line 15—15 of FIG. 13;

DETAILED DESCRIPTION OF THE PREFERRED EMBODIMENTS

Figure 1:
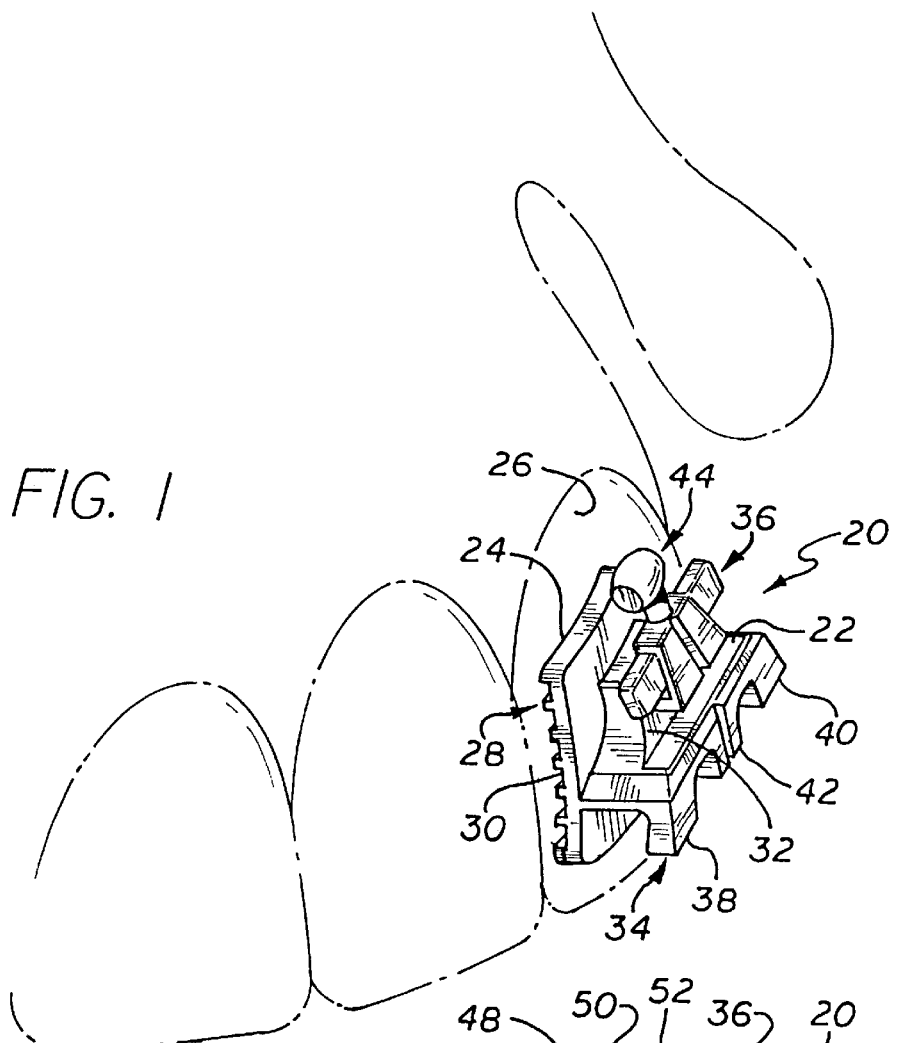
FIG. 1 is a perspective view of a first embodiment of the orthodontic bracket according to the invention illustrating the mounting of the orthodontic bracket on a tooth.

Tooth movement and straightening can be slowed by friction caused by elastic or wire ligature ties on orthodontic brackets, so that it is desirable for such ligature ties to be spaced apart from an archwire particularly during initial and intermediate stages of treatment when the most significant amount of movement and straightening of teeth typically occurs. A number of orthodontic appliances have been constructed to accomplish this, but it can also be desirable for the orthodontic appliance to allow full contact of the ligature ties and archwire, such as may be desirable in the finishing stages of treatment.

As is illustrated in the drawings, the invention is embodied in an orthodontic bracket that permits a ligature tie to be placed on the orthodontic bracket spaced apart from an archwire for the bracket to allow the archwire to slide freely with respect to the orthodontic bracket with minimal friction, and that permits a ligature tie to be placed on the orthodontic bracket with full contact between the ligature tie and archwire, as desired. With reference to FIGS. 1–5, in a first presently preferred embodiment, the present invention provides for an orthodontic bracket 20 for straightening teeth that includes a body 22 having a bonding base 24 adapted for adhering the bracket to a tooth surface 26. The bonding base is currently preferably formed to have a bottom rectangular grid 28 formed by cross-members intersecting at right angles, thereby forming a plurality of rectangular pockets 30, as is described in copending Ser. No. 09/033,370 filed Mar. 2, 1998, the disclosure of which is incorporated by reference herein in its entirety. The body also is preferably formed to include an archwire slot 32 adapted for receiving an archwire, and a plurality of tiewings 34, and a plurality of posts 36 extending in the mesial/distal direction.

Figure 2:
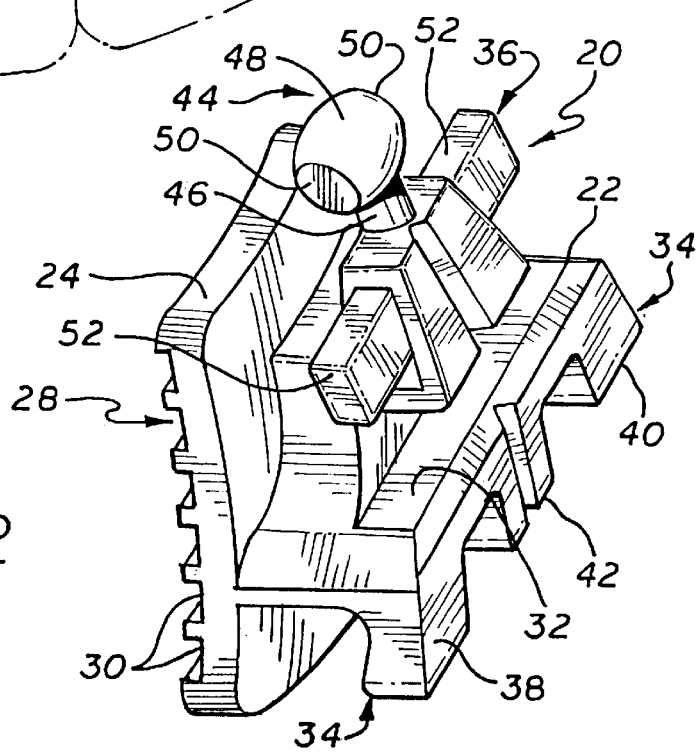
FIG. 2 is an enlarged perspective view of the orthodontic bracket of FIG. 1.

Referring to FIGS. 1, 2 and 4, in a presently preferred aspect of this embodiment, a pair of tiewings 38, 40 are formed on the occlusal side of the body of the bracket, with a center post 42 formed on the body between the two tiewings, for placement reference and ligation of the orthodontic bracket. A hook 44 is also preferably formed on the gingival side of the body of the bracket, for anchorage and ligating the orthodontic bracket. In a presently preferred aspect, the hook comprises a central post 46 extending gingivally from the body of the bracket, with a slightly elongated, rounded or generally egg-shaped knob 48 with flattened ends 50, although the knob may have other similar suitable shapes. Referring to FIGS. 1–4, a pair of posts 52 also are provided on the gingival side of the body of the bracket, extending in the mesial/distal direction of the orthodontic bracket, to assist the orthodontist in bracket placement, and to allow the orthodontist to direct an elastomeric or wire ligature such as a stainless steel ligature over or under the archwire occupying the archwire slot during treatment, as is desired.

With reference to FIGS. 6–10, in a second presently preferred embodiment, the present invention provides for an orthodontic bracket 60 for straightening teeth that includes a body 62 having a bonding base 64 adapted for adhering the bracket to a tooth surface 66. The bonding base is currently preferably formed to have a bottom rectangular grid 68 formed by cross-members intersecting at right angles, thereby forming a plurality of rectangular pockets 70, as described above. The body also is preferably formed to include an archwire slot 72 adapted for receiving an archwire, and a plurality of tiewings 74, and a plurality of posts 76 extending in the mesial/distal direction.

Figure 6:
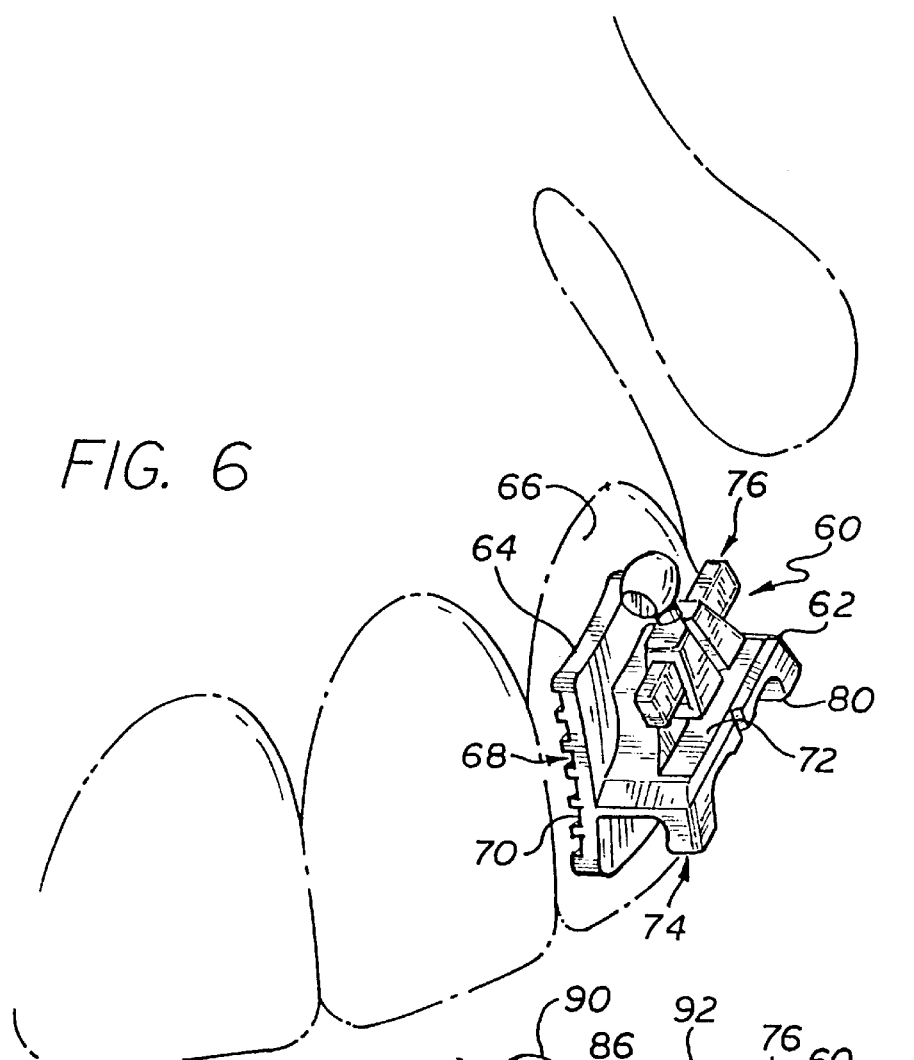
FIG. 6 is a perspective view of a second embodiment of the orthodontic bracket according to the invention illustrating the mounting of the orthodontic bracket on a tooth.
Figure 7:
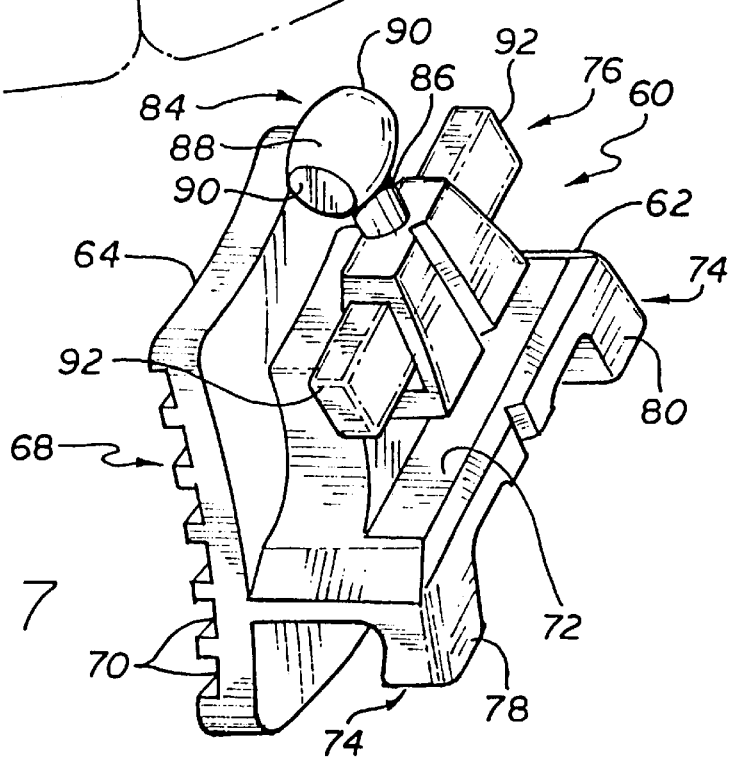
FIG. 7 is an enlarged perspective view of the orthodontic bracket of FIG. 6.

Referring to FIGS. 6, 7 and 9, the second embodiment is similar to that of the first embodiment, in that it provides for a pair of tiewings 78, 80 formed on the occlusal side of the body of the bracket, but in this embodiment no center post is formed between the pair of tiewings. A hook 84 is also formed on the gingival side of the body of the bracket, for anchorage and ligating the orthodontic bracket, and the hook comprises a central post 86 extending gingivally from the body of the bracket, with a slightly elongated, rounded or generally egg-shaped knob 88 with flattened ends 90, as described above. As is best seen in FIGS. 6–9, a pair of posts 92 are provided on the gingival side of the body of the bracket, extending in the mesial/distal direction of the orthodontic bracket.

With reference to FIGS. 11–15, in a third presently preferred embodiment, the present invention provides for an orthodontic bracket 100 for straightening teeth. The orthodontic bracket includes a body 102 having a bonding base 104 adapted for adhering the bracket to a tooth surface 106. The bonding base is currently preferably formed to have a bottom rectangular grid 108 formed by cross-members intersecting at right angles, thereby forming a plurality of rectangular pockets 110, as described above. The body also is also preferably formed to include an archwire slot 112 adapted for receiving an archwire, and a plurality of tiewings 114, and a plurality of posts 116 extending in the mesial/distal direction.

Figure 11:
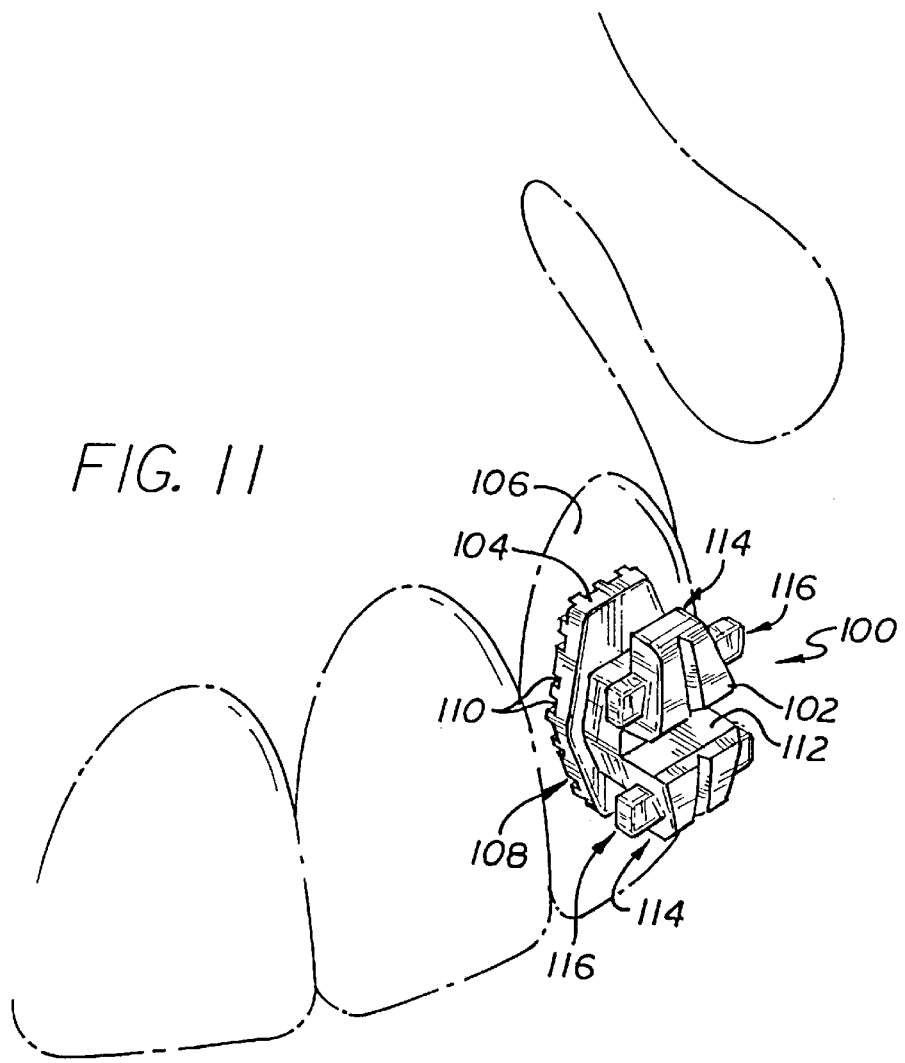
FIG. 11 is a perspective view of a third embodiment of the orthodontic bracket according to the invention illustrating the mounting of the orthodontic bracket on a tooth.
Figure 12:
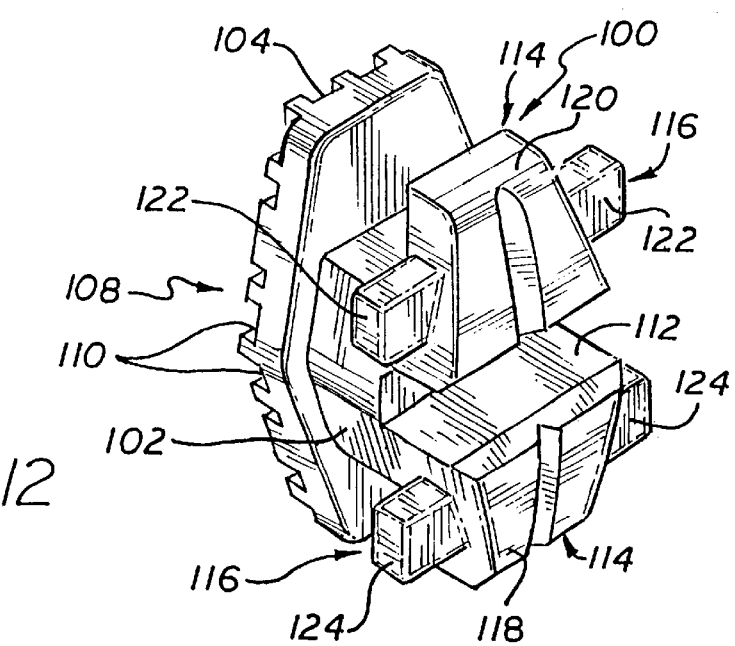
FIG. 12 is an enlarged perspective view of the orthodontic bracket of FIG. 11.

Referring to FIGS. 11, 12 and 14, a tiewing 118 is formed on the occlusal side of the body of the bracket, and an opposing tiewing 120 is formed on the gingival side of the body of the bracket, although alternatively additional pairs of opposing tiewings may also be formed on the occlusal and gingival sides of the bracket. As is best seen in FIGS. 6–9, a pair of posts 122 are provided on the gingival side of the body of the bracket, extending in the mesial/distal direction of the orthodontic bracket, and an opposing pair of posts 124 are provided on the occlusal side of the body of the bracket, extending in the mesial/distal direction of the orthodontic bracket.

Figure 16:
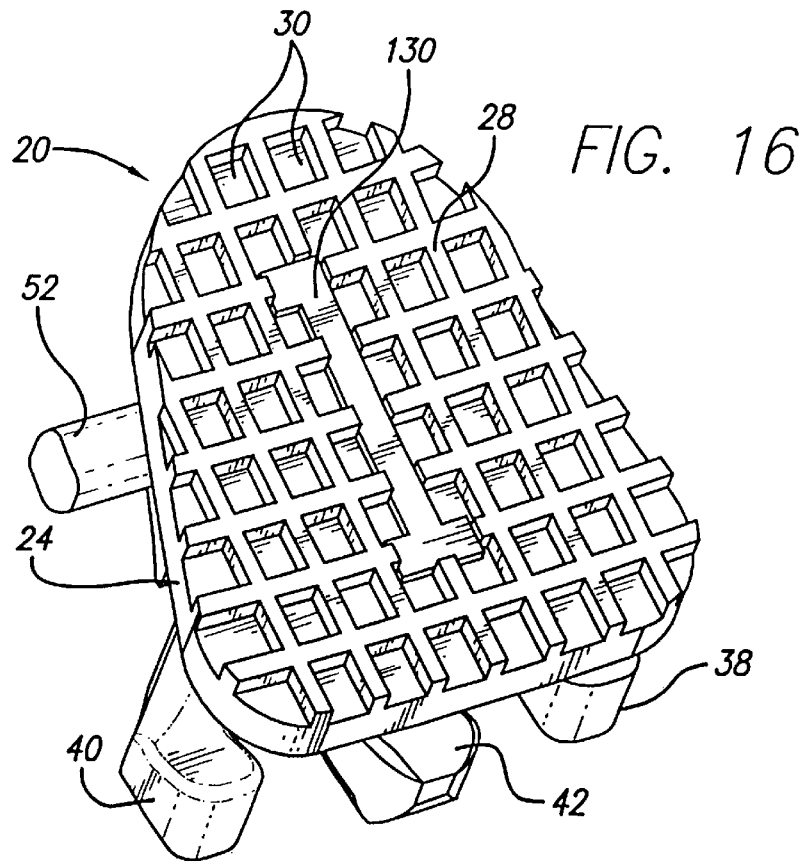
FIG. 16 is a bottom perspective view of an orthodontic bracket according to the invention illustrating the molding of a recessed number on the grid of the bonding base.
Figure 17:
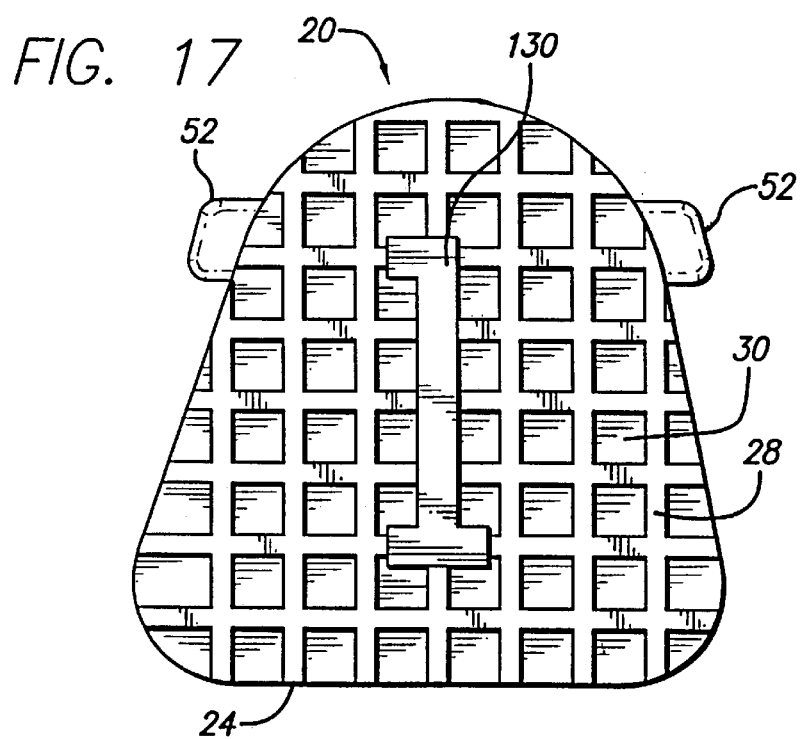
FIG. 17 is a bottom plan view of the base pattern of the orthodontic bracket of FIG. 16.

As is illustrated in FIGS. 16 and 17, another presently preferred aspect of the orthodontic bracket of the invention will be described with regard to the first embodiment of the orthodontic bracket of the invention shown in FIGS. 1–5, although this aspect of the invention can apply equally to the other embodiments of the orthodontic bracket of the invention, and other orthodontic brackets as well. The bonding base 24 of the orthodontic bracket 20 may also advantageously be formed to have a surface defining a molded recessed number 130 within the rectangular grid 28. The molded recessed number can be utilized to identify the preferred location of the tooth upon which the orthodontic bracket is to be placed, as well as the preferred orientation of the orthodontic bracket.

Figure 18:
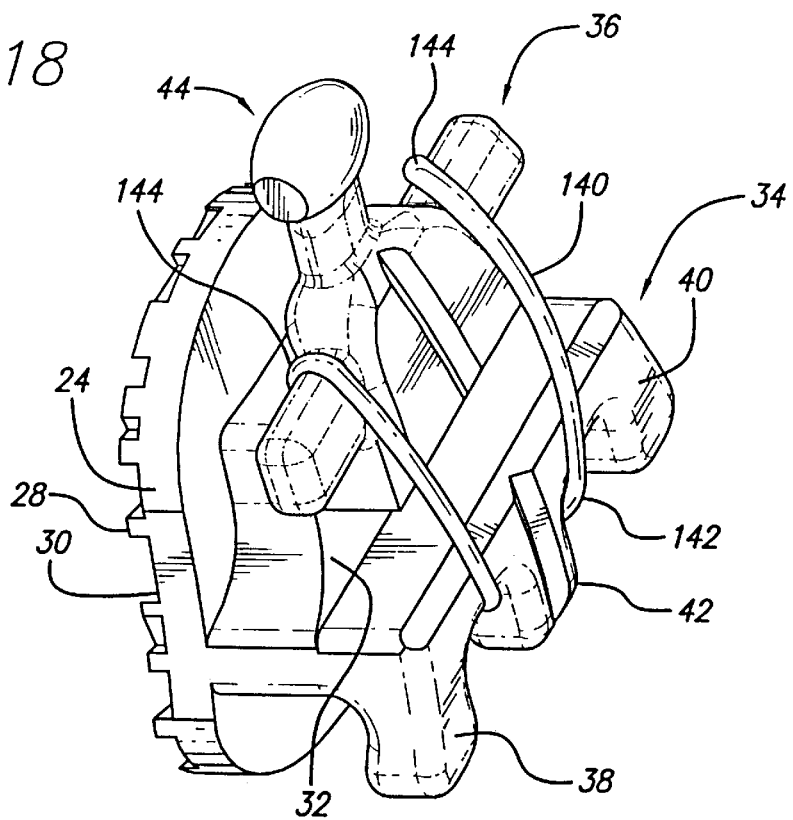
FIG. 18 is a perspective view of the first embodiment of the orthodontic bracket of the invention illustrating the addition of a biocompatible wire clip ligature for the orthodontic bracket.

In another presently preferred aspect of the orthodontic bracket of the invention, as is illustrated in FIG. 18, a biocompatible wire clip 140, formed preferably of a biocompatible metal alloy, such as stainless steel for example, can be placed over the orthodontic bracket to serve as a ligature to retain an archwire in the slot 32. The biocompatible wire clip has a middle portion 142 that can be looped around the center post 42 of the orthodontic bracket, and coiled ends 144 that can be placed over the posts 36 extending in the mesial/distal direction. Alternatively, the middle portion 142 may be adapted to fit over the tiewings 34 of the orthodoontic bracket.

Figure 19:
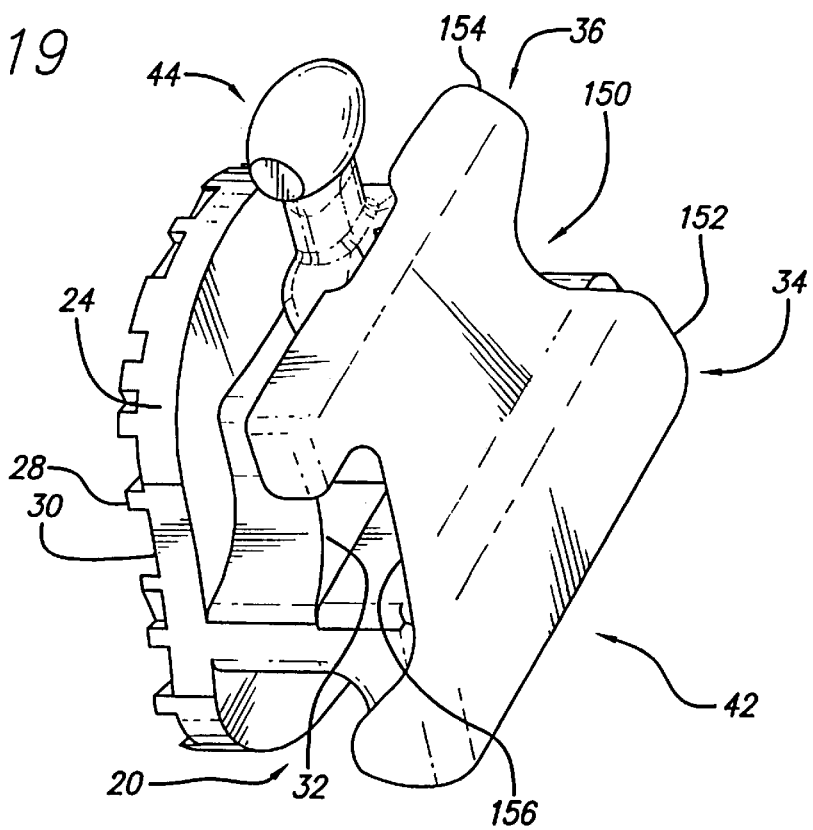
FIG. 19 is a perspective view of the first embodiment of the orthodontic bracket of the invention illustrating the addition of a biocompatible cap ligature for the orthodontic bracket.

As is shown in FIG. 19, in another presently preferred embodiment, a biocompatible cap ligature 150, preferably formed of a biocompatible metal alloy, such as stainless steel for example, may also be placed over the orthodontic bracket to serve as a ligature to retain and archwire in the slot 32. The biocompatible cap ligature includes a first cup-shaped end portion 152 adapted to fit over the tiewings 34 of the orthodontic bracket 20, and a second cup-shaped end portion 154 adapted to fit over the posts 36 extending in the mesial/distal direction.

Figure 20:
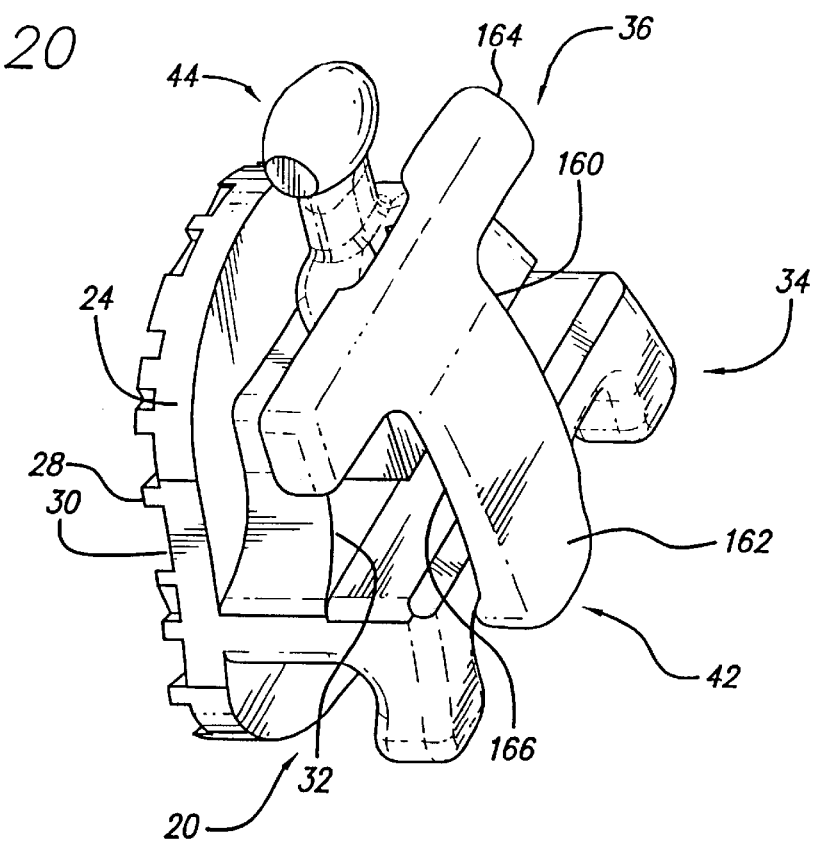
FIG. 20 is a perspective view of the first embodiment of the orthodontic bracket of the invention illustrating an alternate form of the biocompatible cap ligature for the orthodontic bracket.
Figure 21:
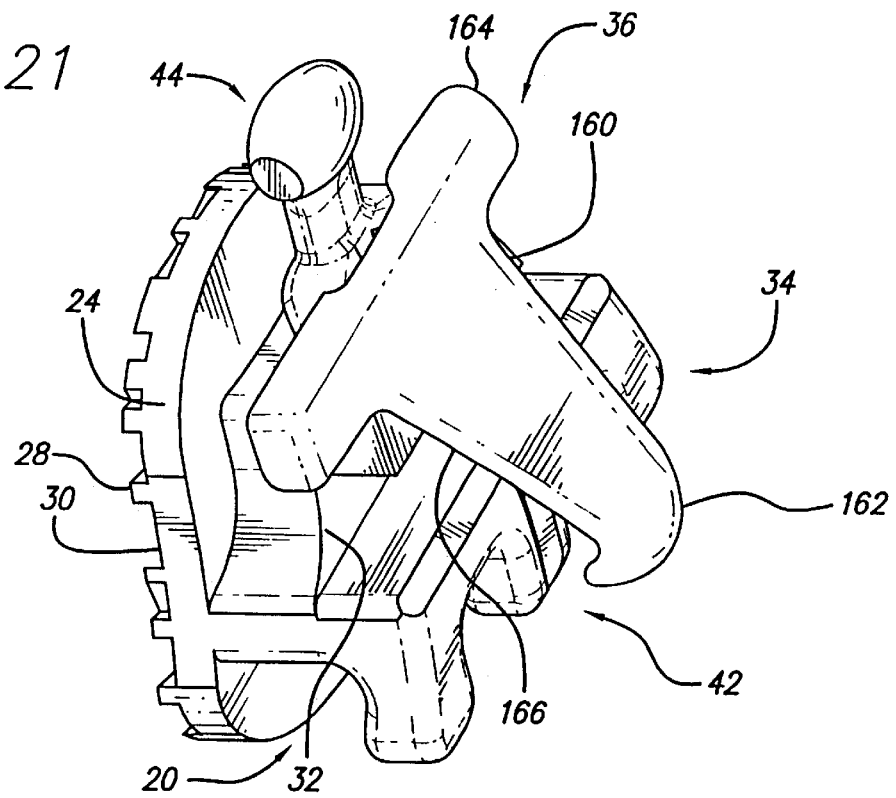
FIG. 21 is a perspective view similar to that of FIG. 20 illustrating the rotation of the biocompatible cap ligature onto or off of the orthodontic bracket.

Referring to FIGS. 20 and 21, in an alternate embodiment, a biocompatible cap ligature 160, preferably formed of a biocompatible metal alloy such as stainless steel for example, may also be placed over the orthodontic bracket to serve as a ligature to retain an archwire in the slot 32. In this alternate embodiment, the biocompatible cap ligature includes a first cup-shaped portion 162 adapted to fit over the center post 42 of the orthodontic bracket, and a second cup-shaped portion 164 adapted to fit over the posts 36 extending in the mesial/distal direction. As can be seen in FIG. 21, the biocompatible cap ligature can be fitted over the orthodontic bracket by placing the second cup-shaped portion over the posts 36 first, and rotating the cap ligature to fit the first cup-shaped portion over the center post 42 between the tiewings.

In a presently preferred aspect of each of the foregoing embodiments, the body of the bracket is comprised of cobalt chromium alloy, although the bracket may alternatively be formed from any other suitable biocompatible metal alloy, such as stainless steel, for example. In each of the foregoing embodiments, the body is preferably a unitary body, and is preferably a unitary metal injection molded body, although the body may also be formed by other suitable techniques such as casting or machining. The body may also be formed as a two piece bracket, with a foil mesh pad bonded to the bonding base for adhering the base to a tooth surface.

It can readily be seen that in the foregoing embodiments, the arrangements of tiewings and mesially/distally extending posts provide for an orthodontic appliance that also allows for the positioning of ligature ties to be spaced apart from the archwire slot of the bracket to reduce frictional engagement between the archwire and the bracket, or to be placed adjacent to the archwire slot of the bracket, for providing full contact of the ligature ties and archwire when desired. The foregoing embodiments of the orthodontic bracket additionally provide for multiple features that can assist the orthodontist in orienting the orthodontic appliance to its optimal position.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An orthodontic bracket for straightening teeth, comprising:

a body having an occlusal side and a gingival side;

a bonding base formed in said body adapted to adhere to a tooth surface;

a surface of said body defining an archwire slot adapted for receiving an archwire;

a pair of tiewings formed on the occlusal side of said body;

a center post formed on said body between said pair of said tiewings; and a plurality of posts formed on said body extending in a mesial/distal direction, whereby a ligature tie can be placed on the orthodontic bracket spaced apart from the archwire slot of the bracket to reduce frictional engagement between the archwire and the orthodontic bracket, or can be placed adjacent to the archwire slot of the bracket, for providing full contact of the ligature tie and archwire to increase frictional engagement between the archwire and the orthodontic bracket.

2. The orthodontic bracket of claim 1, further comprising a hook formed on the gingival side of the body.

3. The orthodontic bracket of claim 1, wherein said plurality of posts are formed on the gingival side of the body.

4. The orthodontic bracket of claim 1, wherein said body is formed of a biocompatible metal alloy.

5. The orthodontic bracket of claim 1, wherein said body is formed of cobalt chromium alloy.

6. The orthodontic bracket of claim 1, further comprising a biocompatible wire coil ligature having coiled ends and a middle portion, said coiled ends adapted to fit over said plurality of posts formed on said body extending in a mesial/distal direction, and said middle portion adapted to fit over said center post.

7. The orthodontic bracket of claim 1, further comprising a biocompatible cap ligature having a first cup-shaped end portion and a second cup-shaped end portion, said first cup-shaped end portion adapted to fit over said plurality of tiewings, and said second cup-shaped end portion adapted to fit over said plurality of posts formed on said body extending in a mesial/distal direction.

8. The orthodontic bracket of claim 1, further comprising a biocompatible cap ligature having a first cup-shaped end portion and a second cup-shaped end portion, said first cup-shaped end portion adapted to fit over said center post, and said second cup-shaped end portion adapted to fit over said plurality of posts formed on said body extending in a mesial/distal direction.

9. The orthodontic bracket of claim 1, wherein said bonding base has a surface defining a molded recessed number for identification of a location of a tooth upon which the orthodontic bracket is to be mounted.

10. An orthodontic bracket for straightening teeth, comprising:
a body having an occlusal side and a gingival side;
a bonding base formed in said body adapted to adhere to a tooth surface;
a surface of said body defining an archwire slot adapted for receiving an archwire;
a plurality of tiewings formed on said body; and
a plurality of posts formed on the occlusal and gingival sides of the body, said plurality of posts extending in a mesial/distal direction, whereby a ligature tie can be placed on the orthodontic bracket spaced apart from the archwire slot of the bracket to reduce frictional engagement between the archwire and the orthodontic bracket, or can be placed adjacent to the archwire slot of the bracket, for providing full contact of the ligature tie and archwire to increase frictional engagement between the archwire and the orthodontic bracket.

11. The orthodontic bracket of claim 10, wherein said plurality of tiewings comprises a plurality of tiewings formed on the occlusal and gingival sides of the body.

12. An orthodontic bracket for straightening teeth, comprising:
a body having an occlusal side and a gingival side;
a bonding base formed in said body adapted to adhere to a tooth surface;
a surface of said body defining an archwire slot adapted for receiving an archwire;
a pair of tiewings formed on the occlusal side of said body;
a center post formed on said body between said pair of said tiewings adapted for placement reference and ligation;
a hook formed on the gingival side of the body adapted for anchorage and ligating; and
a plurality of posts formed on the gingival side of said body extending in a mesial/distal direction adapted to direct a ligature over or under the archwire in the archwire slot, whereby a ligature tie can be placed on the orthodontic bracket spaced apart from the archwire slot of the bracket to reduce frictional engagement between the archwire and the orthodontic bracket, or can be placed adjacent to the archwire slot of the bracket, for providing full contact of the ligature tie and archwire to increase frictional engagement between the archwire and the orthodontic bracket.

13. The orthodontic bracket of claim 12, wherein said body is formed of a biocompatible metal alloy.

14. The orthodontic bracket of claim 12, wherein said body is formed of cobalt chromium alloy.

15. The orthodontic bracket of claim 12, further comprising a biocompatible wire coil ligature having coiled ends and a middle portion, said coiled ends adapted to fit over said plurality of posts formed on said body extending in a mesial/distal direction, and said middle portion adapted to fit over said center post.

16. The orthodontic bracket of claim 12, further comprising a biocompatible cap ligature having a first cup-shaped end portion and a second cup-shaped end portion, said first cup-shaped end portion adapted to fit over said plurality of tiewings, and said second cup-shaped end portion adapted to fit over said plurality of posts formed on said body extending in a mesial/distal direction.

17. The orthodontic bracket of claim 12, further comprising a biocompatible cap ligature having a first cup-shaped end portion and a second cup-shaped end portion, said first cup-shaped end portion adapted to fit over said center post, and said second cup-shaped end portion adapted to fit over said plurality of posts formed on said body extending in a mesial/distal direction.

18. The orthodontic bracket of claim 12, wherein said bonding base has a surface defining a molded recessed number for identification of a location of a tooth upon which the orthodontic bracket is to be mounted.

19. An orthodontic bracket for straightening teeth, comprising:
a body having an occlusal side and a gingival side;
a bonding base formed in said body adapted to adhere to a tooth surface;
a surface of said body defining an archwire slot adapted for receiving an archwire;
a plurality of tiewings formed on the occlusal side of said body;
a hook formed on the gingival side of said body for anchorage and ligating of the orthodontic bracket; and
a plurality of posts formed on the gingival side of said body extending in a mesial/distal direction adapted to direct a ligature over or under the archwire in the archwire slot, whereby a ligature tie can be placed on the orthodontic bracket spaced apart from the archwire slot of the bracket to reduce frictional engagement between the archwire and the orthodontic bracket, or can be placed adjacent to the archwire slot of the bracket, for providing full contact of the ligature tie and archwire to increase frictional engagement between the archwire and the orthodontic bracket.

20. The orthodontic bracket of claim 19, wherein said body is formed of a biocompatible metal alloy.

21. The orthodontic bracket of claim 19, wherein said body is formed of cobalt chromium alloy.

22. The orthodontic bracket of claim 19, wherein said bonding base has a surface defining a molded recessed number for identification of a location of a tooth upon which the orthodontic bracket is to be mounted.

23. An orthodontic bracket for straightening teeth, comprising:

a body having an occlusal side and a gingival side;

a bonding base formed in said body adapted to adhere to a tooth surface;

a surface of said body defining an archwire slot adapted for receiving an archwire;

a plurality of tiewings formed on the occlusal side of said body;

a plurality of tiewings formed on the gingival side of said body; and a plurality of posts formed on said body extending in a mesial/distal direction adapted to direct a ligature over or under the archwire occupying the archwire slot, whereby a ligature tie can be placed on the orthodontic bracket spaced apart from the archwire slot of the bracket to reduce frictional engagement between the archwire and the orthodontic bracket, or can be placed adjacent to the archwire slot of the bracket, for providing full contact of the ligature tie and archwire to increase frictional engagement between the archwire and the orthodontic bracket.

24. The orthodontic bracket of claim 23, wherein said body is formed of a biocompatible metal alloy.

25. The orthodontic bracket of claim 23, wherein said body is formed of cobalt chromium alloy.

26. The orthodontic bracket of claim 23, wherein said bonding base has a surface defining a molded recessed number for identification of a location of a tooth upon which the orthodontic bracket is to be mounted.

27. An orthodontic bracket for straightening teeth, comprising:

a body having an occlusal side and a gingival side;

a bonding base formed in said body adapted to adhere to a tooth surface;

a surface of said body defining an archwire slot adapted for receiving an archwire;

a plurality of tiewings formed on the occlusal and gingival sides of said body;

a plurality of posts formed on the occlusal and gingival sides of said body extending in a mesial/distal direction adapted to direct a ligature over or under the archwire occupying the archwire slot, whereby a ligature tie can be placed on the orthodontic bracket spaced apart from the archwire slot of the bracket to reduce frictional engagement between the archwire and the orthodontic bracket, or can be placed adjacent to the archwire slot of the bracket, for providing full contact of the ligature tie and archwire to increase frictional engagement between the archwire and the orthodontic bracket.

\* \* \* \* \*